United States Patent
Burgio

[11] Patent Number: 6,126,443
[45] Date of Patent: Oct. 3, 2000

[54] MEDICATION DELIVERY TRAY

[75] Inventor: Paul A. Burgio, Grant, Minn.

[73] Assignee: 3M Innovative Properties Company, St. Paul, Minn.

[21] Appl. No.: 09/217,765

[22] Filed: Dec. 21, 1998

Related U.S. Application Data

[63] Continuation-in-part of application No. 09/133,199, Aug. 13, 1998, abandoned.

[51] Int. Cl.⁷ ..................................................... A61C 5/00
[52] U.S. Cl. .................................. 433/215; 433/80; 433/6
[58] Field of Search .................................. 433/6, 80, 24, 433/215, 216, 229

[56] References Cited

U.S. PATENT DOCUMENTS

| | | |
|---|---|---|
| 2,257,709 | 9/1941 | Anderson . |
| 2,963,786 | 12/1960 | Browning ..................................... 32/17 |
| 3,073,300 | 1/1963 | Berghash ................................. 128/136 |
| 3,312,218 | 4/1967 | Jacobs ..................................... 128/136 |
| 3,379,193 | 4/1968 | Monaghan ............................... 128/136 |
| 3,496,936 | 2/1970 | Gores ....................................... 128/136 |
| 3,527,219 | 9/1970 | Greenberg . |
| 3,624,909 | 12/1971 | Greenberg ..................................... 32/40 |
| 3,688,406 | 9/1972 | Porter et al. ................................. 32/40 |
| 4,044,762 | 8/1977 | Jacobs ..................................... 128/136 |
| 4,063,552 | 12/1977 | Going et al. ............................. 128/136 |
| 4,064,628 | 12/1977 | Weitzman ..................................... 32/14 |
| 4,138,814 | 2/1979 | Weitzman ..................................... 32/14 |
| 4,368,040 | 1/1983 | Weissman ................................. 433/36 |
| 4,401,616 | 8/1983 | Wagner ..................................... 264/138 |
| 4,569,342 | 2/1986 | von Nostitz ............................. 128/136 |
| 4,657,508 | 4/1987 | Dellinger ................................... 433/24 |
| 4,776,792 | 10/1988 | Wagner et al. ............................. 433/71 |
| 5,085,585 | 2/1992 | Zimble ....................................... 433/80 |
| 5,165,424 | 11/1992 | Silverman ............................... 128/861 |
| 5,460,527 | 10/1995 | Kittelsen . |
| 5,536,168 | 7/1996 | Bourke .................................. 433/24 X |
| 5,575,655 | 11/1996 | Darnell .................................. 433/80 X |
| 5,702,251 | 12/1997 | McClintock, II .......................... 433/80 |
| 5,707,235 | 1/1998 | Knutson .................................. 433/213 |
| 5,816,802 | 10/1998 | Montgomery ............................. 433/80 |
| 5,842,860 | 12/1998 | Funt .......................................... 433/80 |
| 5,863,202 | 1/1999 | Fontenot et al. ........................ 433/215 |

FOREIGN PATENT DOCUMENTS

| | | |
|---|---|---|
| 2 002 637 | 2/1979 | United Kingdom . |
| WO 98/30381 | 7/1998 | WIPO . |

*Primary Examiner*—Nicholas D. Lucchesi
*Attorney, Agent, or Firm*—James D. Christoff

[57] ABSTRACT

A medication delivery tray provides a controlled release of medication to target dental structures in the mouth, such as the teeth and/or gingiva, while maintaining a high concentration of the active chemical over an extended period of time. The medication delivery tray includes a dental tray having a base, a buccal wall and a lingual wall defining an inner surface. At least one medication reservoir is located on the dental tray. Each medication reservoir includes a plurality of discrete support members projecting away from the medication reservoir to engage the dental structure of the patient. The support members are arranged to resist the flow of medication from the medication reservoir in a gingival direction. Each medication reservoir extends over the teeth and/or gum tissue of the patient when the medication delivery tray is placed over the patient's teeth.

29 Claims, 5 Drawing Sheets

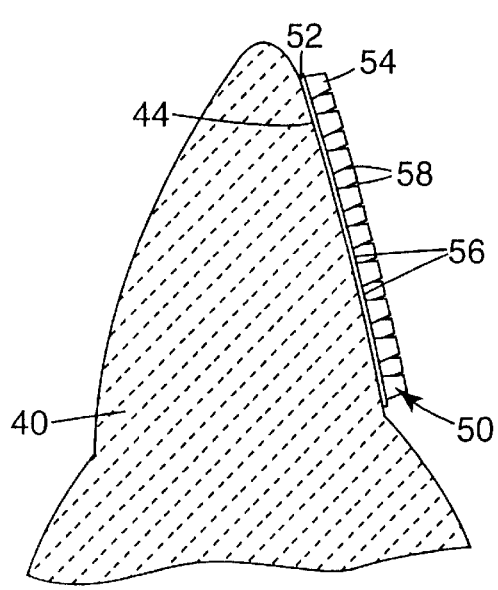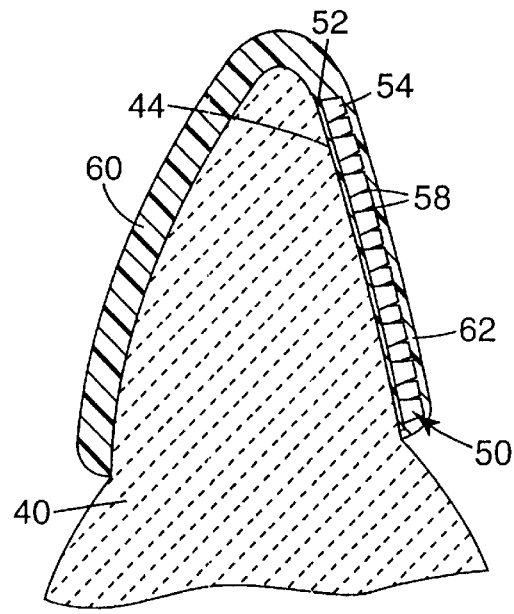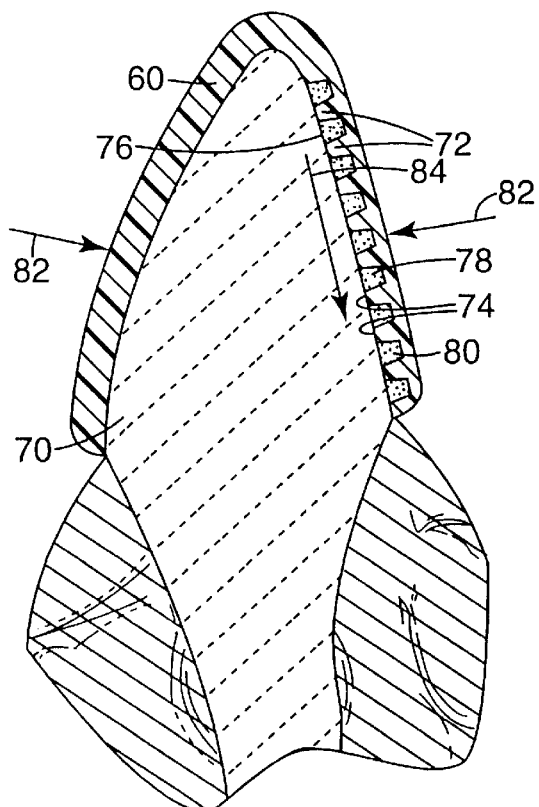

MEDICATION DELIVERY TRAY

This application is a continuation-in-part of U.S. Ser. No. 09/133,199 filed Aug. 13, 1998 now abandoned.

FIELD OF THE INVENTION

The present invention is directed to a medication delivery tray for applying medication to the teeth and/or gum tissue of a patient, and in particular, to medication delivery trays having one or more medication reservoirs that include a plurality of support members which restrict the flow of the medication and resist compression of the medication reservoirs.

BACKGROUND OF THE INVENTION

Dental trays are commonly used to apply medication to the teeth and/or gum tissue of patients. The movement of the tongue, muscles of the mouth and opposing dentition against the dental tray, however, create hydrodynamic forces that causes water or saliva and the medication to move. The primary movement is from the lingual to buccolabial side of the arch, and out over the gingival edge of the dental tray. A secondary movement is created along the length of the recess of the dental tray and out the distal ends of the tray. Consequently, the medication tends to be expelled from the tray and swallowed by the patient in a relatively short period of time.

U.S. Pat. No. 2,257,709 (Anderson) discloses a dental appliance that defines a closed chamber around the teeth. The dental appliance includes a plurality of fingers that create a massaging or rubbing action against the teeth. A cleansing preparation can be applied to the chamber so that it will be flushed in and out around the fingers to aid in the cleansing and massaging actions. A plunger action from the hydrodynamic forces in the mouth is thus created in the chamber, which forces the cleansing and treating material into and out of all cavities, spaces between the teeth, and even between the marginal edges of the gums and the teeth. Although the flaps on the dental appliance theoretically adhere to the gums, in practice, the plunger action disclosed in Anderson likely forces the cleansing preparation into the patient's mouth, where it is swallowed.

U.S. Pat. No. 3,527,219 (Greenberg) discloses a dental tray having a foam or open cell insert for carrying a medication. The hydrodynamic forces within the mouth compress the foam to create a pumping action that expels the medication from the dental tray.

U.S. Pat. No. 5,460,527 (Kittelsen) discloses a composite dental bleaching tray having a plurality of pockets on an inner surface to receive and hold a bleaching gel for bleaching teeth. Similarly, U.S. Pat. No. 5,234,342 (Fischer) discloses a method of making a dental tray with reservoirs formed opposite the teeth. The pockets of Kittelsen and the reservoirs of Fischer are both subject to the hydrodynamic forces of the mouth that cause the medication to be expelled from the dental tray.

Both the thickness and the flexibility of the material from which the tray is constructed are significant factors in the ability of the tray to resist hydrodynamic forces in the mouth. Dental trays made from material of about 2 millimeters (0.080 inches) to about 3.8 millimeters (0.150 inches) thick tend to be better at resisting hydrodynamic forces than dental trays made from thinner materials. On the other hand, dental professionals know that patients are more likely to wear a tray that is less obtrusive in the mouth. Dental trays made from sheet material of about 1 millimeter (0.040 inches) thick are far more comfortable to wear. Unfortunately, a dental tray of this thickness is more flexible and therefore tends to lack the mechanical stability to resist hydrodynamic forces.

When dental trays are used for teeth bleaching at home, the patient places an amount of a bleaching solution into each area of a dental tray for each tooth to be bleached. The tray is then placed in the mouth. Often, the bleaching solution is changed every 0.5 to 2.5 hours, and the dental tray is removed during meals. Sometimes a recommendation is made to wear the dental tray overnight. The efficacy of the bleaching procedure depends upon such factors as type and intensity of the stain, the bleaching agent contact time on the teeth, the amount of available active ingredient in the bleaching agent as well as patient acceptance and adherence to the procedure.

As can be appreciated, the cost for the teeth bleaching procedure is substantially less when the procedure is carried out at the patient's home rather than in the dental office, since the practitioner's time associated with the procedure is reduced. Moreover, patient discomfort associated with home-use tooth bleaching techniques both during and after treatment is reportedly less than that associated with conventional in-office bleaching.

Notwithstanding the foregoing advantages, there remain some important disadvantages to conventional home-use bleaching products and techniques. For example, the hydrodynamic forces in the mouth cause the volume of the bleaching agent in the tray to diminish rapidly over time, thereby decreasing the amount of active ingredient available for tooth bleaching. Test results show that after 30 minutes, less than 50% of the original quantity of bleaching agent was available for bleaching activity. After one hour, less than 25% of the bleaching agent was available for bleaching activity on the tooth surface (April 1997 Clinical Research Associates Newsletter). Thus, existing bleaching agents typically need to be replenished about every 15 to 30 minutes in order to maintain the most efficacious dosage of bleaching agent in contact with the tooth.

Unfortunately, the daytime schedules of many patients do not easily accommodate periodic, continuous replenishment of the bleaching agent. In addition, periodically replenishing the bleaching agent during the night is unrealistic for many patients. Since patient adherence to the procedure determines the ultimate success of the tooth bleaching treatment, the need to constantly replenish the dental bleaching agent is a major obstruction that limits the success of the treatment.

BRIEF SUMMARY OF THE INVENTION

The present invention is directed to a medication delivery tray that provides a controlled release of medication to target dental structures in the mouth, such as the teeth and/or gingiva, while maintaining a high concentration of the active chemical for an extended period of time.

The medication delivery tray includes a dental tray having a base, a buccal wall and a lingual wall defining an inner surface. At least one medication reservoir is located on the dental tray. The medication reservoir includes a plurality of discrete support members projecting away from the medication reservoir to engage the dental structure of the patient. The support members are arranged to resist the flow of medication from the medication reservoir in a gingival direction. A custom dental tray is typically preferred.

The hydrodynamic forces in the mouth typically propel the medication in a direction normal to the base toward a gingival edge of one of the tray walls. A secondary motion is indicated along the length of the tray. The support members resist the hydrodynamic forces by minimizing the compression of the medication reservoirs. The support members are preferably arranged to form tortuous paths that resist the flow of medication in these directions. The support members are optionally constructed of a hydrophilic material that assists in retaining the medication within the medication reservoir.

For some embodiments, such as embodiments that include a dental bleach agent, the medication is activated with water and/or saliva. Although the support members resist the flow of medication out of the present dental tray, a limited amount of saliva is permitted to enter the tray to activate the medication. As the medication reacts with the dental structure, additional saliva enters the tray to provide a fresh surface of activated medication.

In one embodiment, the medication reservoirs comprise an applique embedded in a custom dental tray. The applique may be constructed from a hydrophilic material. In another embodiment, the medication reservoirs are formed integrally with a custom dental tray. The medication reservoirs are typically located on the inner surface of the medication delivery tray. The medication reservoir may extend over substantially the entire inner surface of the dental tray.

The support members may be selected from a group consisting of cubes, rods, cones, truncated cones, pyramids, truncated pyramids, semispheres, cylinders, nail heads, or mushroom-shaped members. In one embodiment, the support members are arranged to define a tortuous path. The tortuous path resists the flow of medication in a direction along at least one of a mesial-distal direction and a gingival direction.

The medication reservoirs are positioned to extend over at least one tooth and/or at least a portion of the gum tissue when the medication delivery tray is retained by the dental structure of a patient. For dental bleaching applications, the medication reservoirs are positioned to extend over the buccolabial surfaces of the teeth.

The present invention is also directed to a kit for forming a medication delivery tray from a thermoplastic material molded over a dental structure or a model thereof. The kit includes at least one applique attachable to the dental structure or model thereof for forming at least one medication reservoir in the thermoplastic material. Each of the appliques defines a plurality of support members that are arranged to resist the flow of medication from the medication reservoir in a gingival direction.

An alternate kit includes a sheet member comprising a backing layer and a plurality of support members projecting from the backing layer. The support members are arranged to resist the flow in a gingival direction of medication from the medication delivery tray formed therefrom.

The present invention is also directed to a method of making a medication delivery tray for delivering medication to dental structures of a patient. The method includes the acts of applying at least one applique to a model of the patient's dental structure. Each applique defines a plurality of support members arranged to resist the flow of medication from the medication reservoir in a gingival direction. A custom dental tray is formed over the model and each applique from a thermoplastic material. The custom dental tray is removed from the model. The method also includes the acts of applying a medication to the medication reservoirs and applying the custom mouth tray to the patient's dental structure such that the medication reservoirs are positioned opposite at least a portion of the dental structure.

In an alternate method, a sheet member comprising a backing layer and a plurality of support members projecting from the backing layer is prepared. A custom dental tray is formed directly over the patient's dental structure or a model thereof from the sheet member such that the support members are arranged to resist the flow of medication from the medication delivery tray in a gingival direction. The custom dental tray is removed from the dental structure or model thereof.

Another aspect of the invention is also directed to a method of making a medication delivery tray for delivering medication to dental structures of a patient. In this aspect, the method comprises the acts of providing a model of at least a portion of a dental arch and applying on applique to a plurality of teeth of the model. A custom dental tray is then formed over the model and the applique.

BRIEF DESCRIPTION OF THE SEVERAL VIEWS OF THE DRAWING

FIG. 3 is an enlarged side sectional view of the casting and one of the appliques shown in FIG. 2.

FIG. 4 is an enlarged side sectional view of the present medication delivery tray being formed over the casting and applique of FIG. 3.

FIG. 5 is an enlarged side sectional view of the medication delivery tray shown in FIG. 4 after removal from the casting and once engaged with a tooth.

DETAILED DESCRIPTION OF THE PREFERRED EMBODIMENTS

Figure 1:
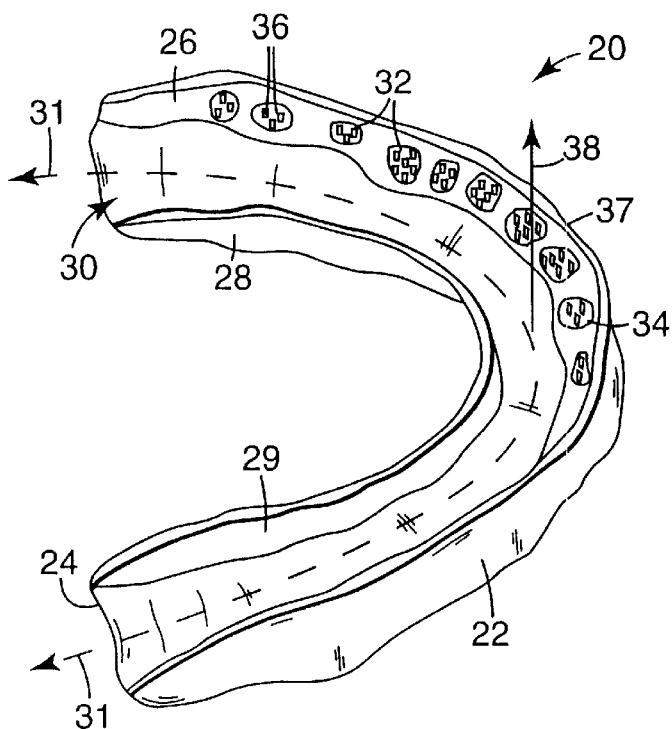
FIG. 1 is a perspective view of a medication delivery tray in accordance with certain embodiments of the present invention.

FIG. 1 is a perspective view of a medication delivery tray 20 in accordance with the present invention. The medication delivery tray 20 comprises a custom dental tray 22 having a base 24, a buccal wall 26 and a lingual wall 28. The medication delivery tray 20 has an inner surface 29 that defines a channel 30. In the illustrated embodiment, a plurality of medication reservoirs 32 are located on the buccal wall 26, although they may be located anywhere on the medication delivery tray 20. In some of the embodiments discussed below, a single medication reservoir extends across all or across a major extent of the inner surface 29.

Each of the medication reservoirs 32 defines a recess 34 containing a plurality of support members 36 projecting outwardly therefrom. The support members 36 next to the buccal wall 26 project away from the recess 34 in a lingual direction to engage with the dental structures of a patient (see FIGS. 5 and 8). However, if support members are located next to the base 24 or the lingual wall 28, those support members would extend in a gingival direction or in a buccolabial direction respectively.

Custom dental tray refers to a dental tray made using a mold, casting or other model of the patient's dental structures. Custom dental tray also refers to a dental tray that is made using digital data representative of the patient's dental structure. A further discussion of the use of digital data is set out below. Dental structures refer to the teeth and/or gum tissues.

Figure 2:
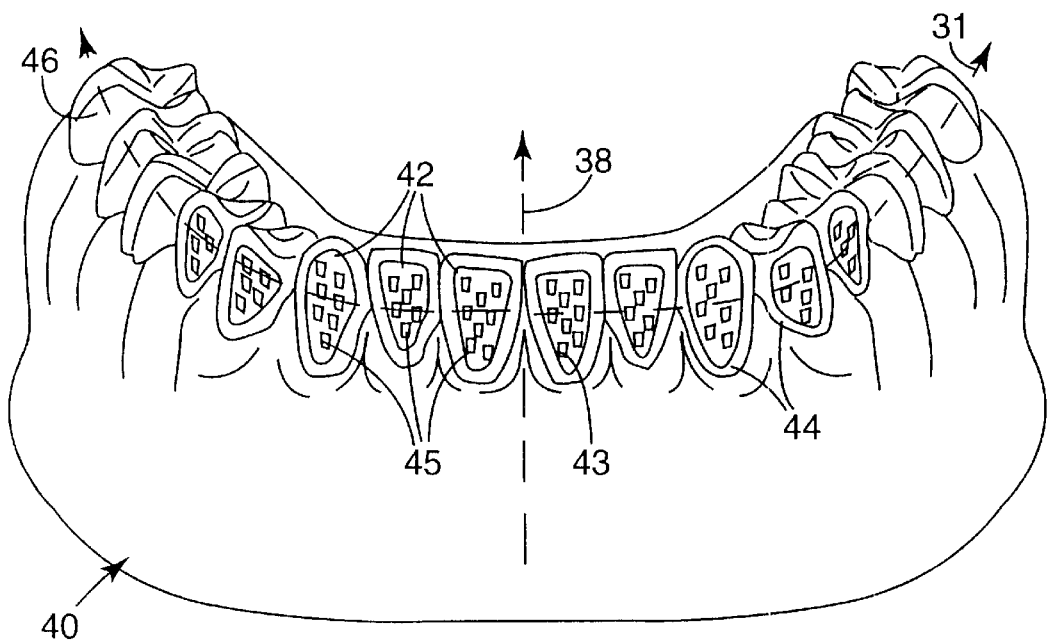
FIG. 2 is a perspective view of an exemplary casting of a patient's dental structure containing appliques in accordance with certain embodiments of the present invention.

FIG. 2 is a perspective view of a model or casting 40 formed from an alginate impression of a patient's dental structure. The casting 40 may be made from either the teeth and/or gum tissues of the patient's upper or lower jaw. In one embodiment, a number of appliques 42 are applied to various surfaces of the casting 40 using an adhesive or other suitable means. The appliques 42 include a series of discrete, free standing protrusions 45 that define the support members 36 (FIG. 1) during the forming process. That is, the protrusions 45 either serve as the support members 36 in the medication delivery tray or the protrusions 45 act as a mold for forming the support members 36, as will be discussed below.

In the embodiment illustrated in FIG. 2, the appliques 42 are applied to the casting 40 in regions corresponding to the buccolabial surfaces 44 of the teeth 46. The appliques 42 can also be applied to portions of the casting 40 corresponding to the lingual tooth surfaces and/or portions of the gum tissue. A medication delivery tray 20 such as illustrated in FIG. 1 is then thermoformed or vacuum formed over the casting 40 and the appliques 42.

When the medication delivery tray 20 is placed in a patient's mouth, the hydrodynamic forces tend to force any medication retained in the tray 20 in directions from the lingual wall 28 to the buccal wall 26, and then in a gingival direction 38 normal to the base 24. Eventually, the medication is expelled from the tray 20 over gingival edge 37, where it mixes with water or saliva and is swallowed by the patient. A secondary movement of medication is created in a mesial-distal direction 31 along the length of the channel 30 of the medication delivery tray 20. The support members 36 minimize the compression of the medication reservoirs 32 by hydrodynamic forces within a patient's mouth. Additionally, the discrete, free standing nature of the support members 36 increases the resistance to fluid movement within the medication delivery tray 20.

With conventional dental trays, the flow of medication out of the tray restricts the in-flow of saliva into the tray. In the present invention, minimizing the compression of the medication reservoirs 32 typically permits a limited amount of saliva to enter the tray 20 over the gingival edge 37, where it mixes with and for some applications activates the medication.

The medication is applied around the discrete, free standing support members 36. The surface tension and viscosity of the medication tends to allow the medication to adhere to the support members 36 and consequently reduce the flow of the medication out of the custom dental tray 22. In one embodiment, the support structures 36 are arranged to define tortuous paths 43. A tortuous path refers to a passageway or conduit that is not substantially straight and extends past the sides of a plurality of support structures 36 in the spaces between the adjacent support structures 36. The tortuous paths are preferably arranged to increase flow resistance in the gingival direction 38 and/or in the mesial-distal direction 31 along the channel 30. To the extent that any segment of the tortuous paths 43 is straight, that segment is preferably skewed with respect to the gingival direction 38 or the mesial-distal direction 31 of the channel 30. In one embodiment, the support members 36 are constructed from a hydrophilic material.

FIG. 3 is a side sectional view of the casting 40 with an applique 50 applied to a surface corresponding to a buccal surface 44 by an adhesive 52. The applique 50 includes a series of protrusions 54 in the shape of truncated cones or pyramids. Optionally, a land area 56 separates each of the protrusions 54 from adjacent protrusions 54. FIG. 4 is a side sectional view of the casting 40 and applique 50 of FIG. 3 during the formation of a medication delivery tray 60. The spaces 58 between the truncated cones or pyramids 54 define a series of support members 72 on an inside surface of the medication delivery tray 60 as the tray 60 is molded. When the medication delivery tray 60 is removed from the casting 40 and applique 50, a lingual-facing portion of the buccal wall 62 has a micro-replicated surface that is an inverse of the protrusions 54 on the applique 50.

The medication delivery tray 20 maybe constructed of a variety of thermoplastic materials, such as polypropylene, rayon, or copolymers of ethylene and vinyl acetate, such as ethylene vinyl acetate (EVA). EVA is commercially available and approved for oral use by the U.S. Food and Drug Administration. These materials are easily thermoformed or vacuum formed over the casting 40 using conventional techniques.

FIG. 5 is a side sectional view of the medication delivery tray 60 shown in FIG. 4 retained by the teeth 70 of a patient. The land areas 56 of the applique 50 correspond to outer ends 74 on each of the support members 72. When engaged with the patient's teeth 70, the outer ends 74 of the support members 72 engage the buccolabial surface 76 of the teeth 70. The regions between the support members 72 define a medication reservoir 78 for receiving a medication 80.

In the embodiment illustrated in FIG. 5, hydrodynamic forces in the general directions of the arrows 82 acting on the medication delivery tray 60 would have a tendency to expel the medication 80 along a gingival reference axis 84. The support members 72, however, resist the pumping action caused by the forces 82 and reduce the flow of medication 80 from the medication delivery tray 60.

The support members 72 can have a variety of geometric shapes in cross section, such as rectangular, circular, semi-circular, triangular, square, hexagonal, and the like. The support members may assume a variety of shapes, such as cones, truncated cones, rods, pyramids, truncated pyramids, cubes, gum drops, cylinders, nail heads or mushroom-shaped members, and the like. The outer ends 74 may be flat, rounded, pointed or a variety of other shapes, as determined by the shape of the spaces between the protrusions 54 and the optional land areas 56. Forming appliques 50 having a micro-replicated surface may be accomplished by using a variety of methods, such as disclosed and U.S. Pat. No. 5,152,917 (Pieper, et al.) and U.S. Pat. No. 5,500,273 (Holmes, et al.).

The support members 72 preferably decrease in transverse cross-sectional area in this embodiment as the outer ends 74 are approached. In general, the number of support members 72 per unit area is preferably in the range of about 78 per square centimeter (500 per square inch) to about 465 per square centimeter (3000 per square inch). However, a higher or lower number of support members 72 per unit area may be optimal in certain circumstances and the optimal number may depend on factors such as the nature of the material used to form the medication delivery tray 60, the characteristics of the medication and the shape, height and diameter of the support members 72. The height of the support members 72 is preferably in the range of about 0.5 millimeters to about 1.5 millimeters, although larger and smaller support members 72 may be used for specific applications, depending upon the viscosity of the medication, the nature of the treatment, the specific dental structure being treated, etc.

Figure 6:
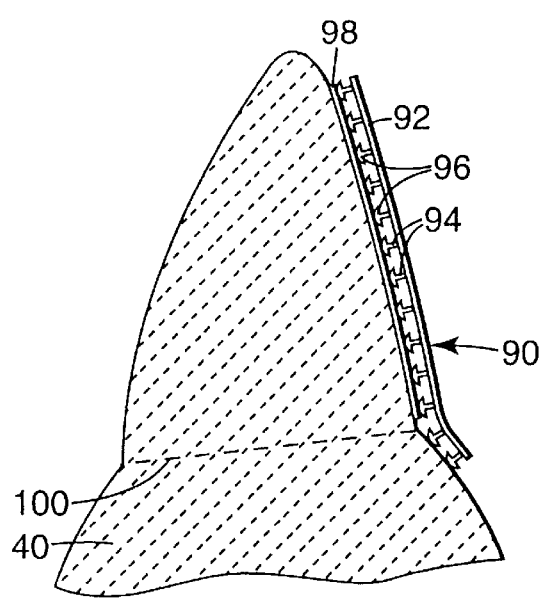
FIG. 6 is an enlarged side sectional view of an alternate applique applied to a tooth casting in accordance with another embodiment of present invention.

FIG. 6 illustrates an alternate applique 90 applied to the casting 40 according to another embodiment of the present invention. The applique 90 includes a plurality of headed protrusions or stems 94 projecting outwardly from a backing 92. Heads 96 of the stems 94 are retained against the casting 40 by an adhesive sheet 98 containing a layer of adhesive on both sides. In the embodiment illustrated in FIG. 6, the applique 90 extends down below the region corresponding to the gingival line 100 on the casting 40. Various manufacturing processes for forming an array of upstanding headed stems integral with a backing are described in U.S. Pat. No. 4,290,174 (Kalleberg), U.S. Pat. No. 4,984,339 (Provost, et al), WO 94/23610 (Miller, et al) and WO 98/30381 (Miller, et al) and PCT/US97/15960 (Kempfer).

Figure 7:
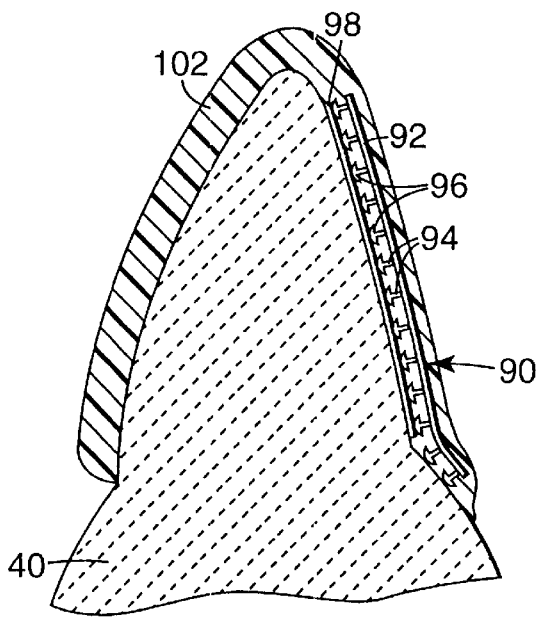
FIG. 7 is an enlarged side sectional view of a medication delivery tray formed over the casting and applique of FIG. 6.

FIG. 7 illustrates the act of thermoforming a medication delivery tray 102 over the applique 90 of FIG. 6. In the embodiment illustrated in FIG. 7, the appliques 90 are embedded within the material forming the medication delivery tray 102. That is, the appliques 90 are integrally molded into the medication delivery tray 102.

Figure 8:
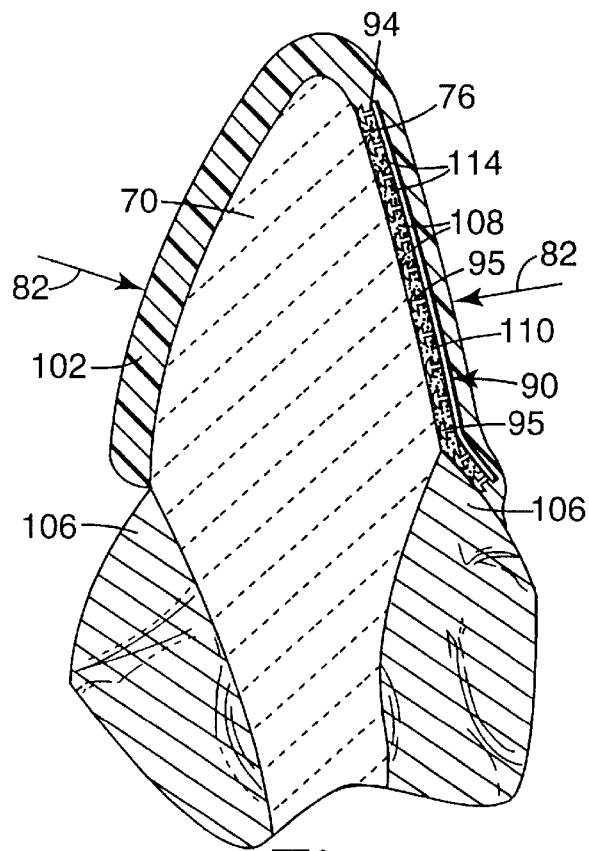
FIG. 8 is an enlarged side sectional view of the medication delivery tray illustrated in FIG. 7 after the tray has been removing from the casting and placed in engagement with a patient's teeth and gum tissue.

FIG. 8 is a side sectional view of the medication delivery tray 102 applied to the teeth 70 and gum tissue 106 of a patient. The headed stems 94 comprise the support members 95 that resist the forces 82. Spaces 108 between the headed stems 94 comprise the medication reservoir 110. The undercut regions of the headed stems 94 aid in retaining medication 114 in the reservoir 110. The outer ends of the headed stems 94 engage with a buccal surface 76 of tooth 70, as well as part of the gum tissue 106. Consequently, the medication 114 may be simultaneously applied to the tooth 70 and the gum tissue 106.

Figure 9:
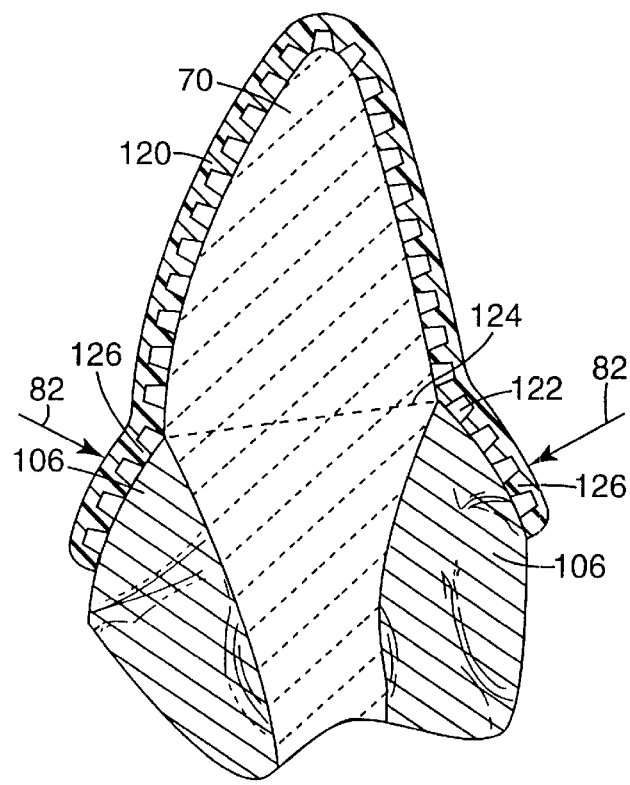
FIG. 9 is an enlarged side sectional view of a medication delivery tray in accordance with another embodiment of the present invention for applying medication to a gum region adjacent to a tooth as well as to the tooth.

FIG. 9 illustrates an alternate medication delivery tray 120 in which the medication reservoirs 122 are located to extend across and engage with both sides of the teeth 70 and a portion of the gum tissue below the gingival line 124. A single continuous medication reservoir 122 may be formed extending over all sides of the teeth 70. Alternatively, discrete medication reservoirs may be located to treat selected areas of the gum tissue 106. When the medication delivery tray 120 is engaged with the teeth 70, the medication reservoir 122 and support members 126 are positioned opposite the teeth 70 and gum tissue 106 to resist compression under the forces 82.

Figure 10:
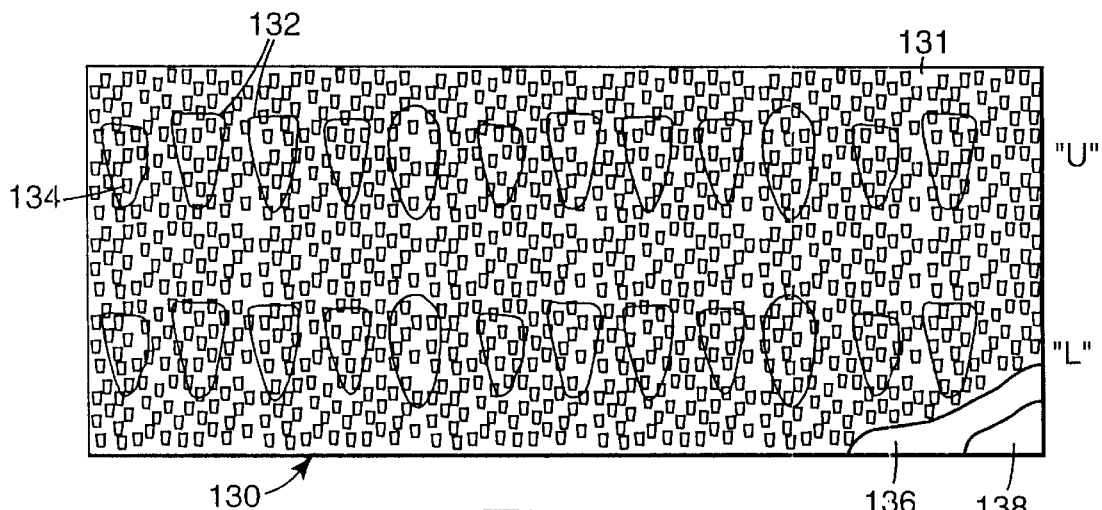
FIG. 10 is an enlarged schematic illustration of a sheet of appliques in accordance with certain embodiments of the present invention.

FIG. 10 is a schematic illustration of a sheet 130 containing a plurality of appliques 132 in accordance with the present invention. After a micro-replicated surface 134 having a number of protrusions is formed on the sheet 130, the appliques are die-cut to the desired shape. In one embodiment, the back surface of the sheet 130 includes a pressure sensitive adhesive 136 covered by a release liner 138. Optionally, the pressure sensitive adhesive 136 comprises a tape having adhesive on both sides. The appliques 132 (which include the adhesive) may be peeled from the release liner 138 and remaining portions of the sheet 130 and applied to a casting 40, as discussed above. In another embodiment, a double-sided adhesive tape extends over the outer ends of the protrusions of each applique and is applied to the casting 40. In yet another embodiment, an adhesive is applied directly to the casting. In this embodiment, either the back surface or the microreplicated surface 134 of the appliques may be attached to the casting.

In one embodiment, a separate medication reservoir is provided for each tooth being treated. Consequently, the appliques 132 are configured for attachment to the portion of the casting corresponding to the teeth. For example, and as shown in FIG. 10, each applique has a shape that generally matches the shape of the buccolabial surface of a typical tooth. Alternatively, the appliques 132 may be configured as elongated strips to engage with portions of the casting corresponding to multiple teeth or large sections of gum tissue. In one embodiment, a single applique extends across substantially all of the teeth on the casting.

Figure 11:
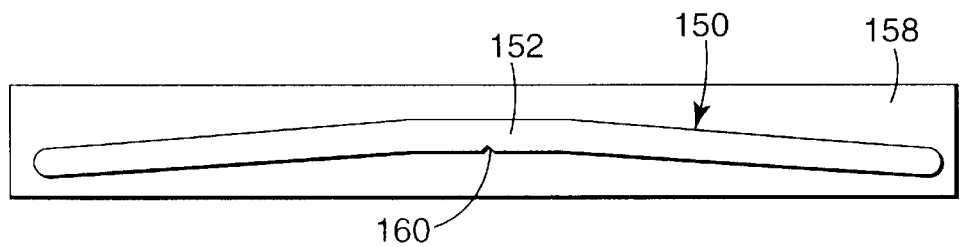
FIG. 11 is a side elevational view of an applique according to another embodiment of the invention, wherein the applique is carried on a release liner.
Figure 12:
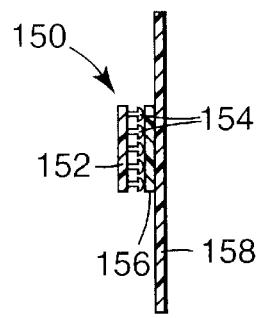
FIG. 12 is an end cross-sectional view (not to scale) of the applique and release liner shown in FIG. 11.

FIGS. 11 and 12 are illustrations of an exemplary applique 150 having an elongated strip configuration. The applique 150 is made of a backing layer 152 and a number or protrusions 154 connected to the backing layer 152. The protrusions 154 are preferably similar to the protrusions 45, 54 or 94 described above. Optionally, the protrusions are made by a micro-replication process. An example of a suitable applique 150 is a die-cut section of the hook side of a polypropylene micro-replicated mechanical fastener, such as No. CS-200 diaper tape from 3M Company.

A layer of adhesive 156 is preferably comprised of a section of tape that is coated on both sides with pressure sensitive adhesive, although other constructions and other types of adhesive are also possible. An example of a suitable adhesive layer is a medical grade double-sided adhesive tape such as no. 1522 from 3M Company. One side of the adhesive 156 is releasably connected to outer ends of the protrusions 154, and the other side of the adhesive is attached to a release liner 158 to facilitate handling of the applique 150. Suitable materials for the release liner 158 include a section of poly(ethylene terephthalate) ("PET") sheeting that is coated with silicone to enhance release of the adhesive.

Figure 13:
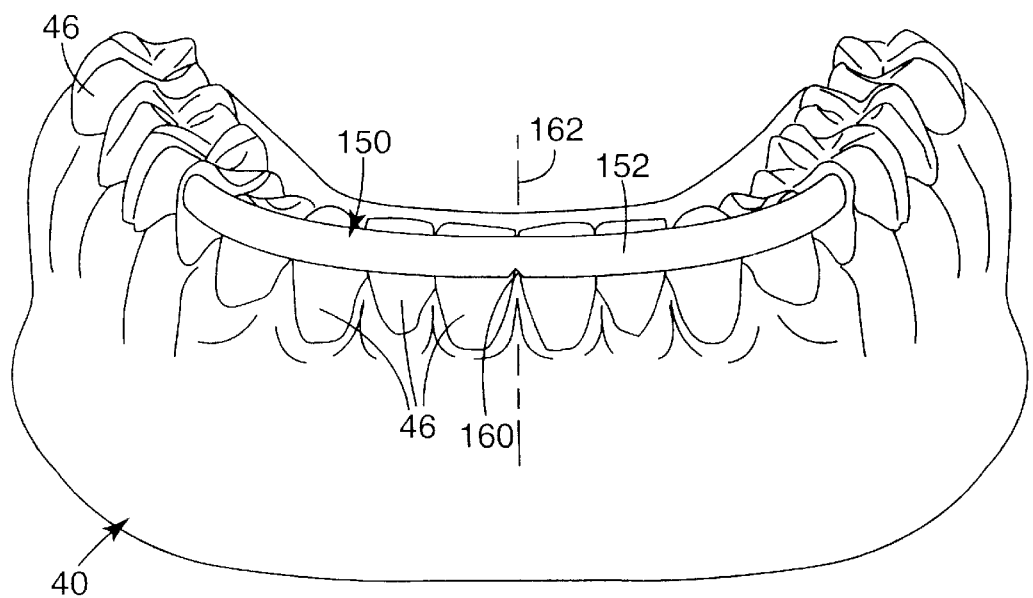
FIG. 13 is a perspective view of a casting of a patient's dental structure along with the applique shown in FIGS. 11 and 12.

In use, the applique 150 and the adhesive 156 are detached from the release liner 158 and trimmed as necessary. The applique 150 and the adhesive 156 may be trimed after initially placed on the casting 40 or alternatively trimmed before detachment from the release liner 158. The applique is trimmed to a length sufficient to extend across all of the tooth surfaces intended to receive medication. Optionally, and as shown in FIG. 13, the applique 150 and the underlying adhesive 156 are trimmed to a length corresponding to a length extending mesially-distally along the dental arch from one of the second bicuspid teeth to the other. However, if the molar teeth are heavily stained, the applique 150 may be somewhat longer in order to extend over the molar tooth surfaces as well.

Preferably, a gingival edge of the applique 150 includes a notch 160 that is located in the center of the applique 150 along its length. When the applique 150 is placed on the casting 40, the practitioner places the notch 160 along the midline (i.e., in the center of the dental arch of the casting 40 in alignment with reference axis 162), so that the applique 150 is properly centered on the casting 40. The notch 160 provides a visual alignment guide to facilitate placement of the applique 150 on the casting 40. Preferably, the applique 150 is aligned to the mid-third of the model teeth 46 as shown in FIG. 13.

Preferably, but not necessarily, the applique 150 is initially curved in a wide arc when attached to the release liner 158 as can be observed by reference to Figure 111. The arc-shaped configuration of the applique 150 facilitates conforming the applique 150 to the buccolabial tooth surfaces of the casting 40 as the applique 150 is attached to the casting 40. Optionally, the practitioner may apply finger pressure to the applique 150 in areas extending over interproximal regions of the dental arch in order to better conform the applique 150 to the curvature of the individual teeth 46.

Next, a dental medication delivery tray is formed over the casting 40 and the applique 150. For example, a sheet of thermoplastic material may be thermoformed or vacuum formed over the casting 40 and the applique 150. Suitable thermoplastic materials include, for example, 0.04 inch (1.0 mm) thick EVA vacuum forming material (catalog no. 089-5003, from Patterson Dental Supply, Inc.). Preferably, the applique 150 both chemically and mechanically bonds to the thermoplastic material in order to remain non-removably affixed in place in the tray.

The resultant dental tray is then removed from the casting 40. Preferably, the adhesive 156 preferentially adheres to the casting 40, so as the tray is pulled from the casting the adhesive 156 detaches from the applique 150 and remains on the casting 40. Medication such as a dental bleaching agent is then applied to the applique 150 in the tray and the tray is then placed over the patient's dental arch.

When the tray is used to whiten teeth, the tray is preferably trimmed with scissors near the gingival margin. The trimmed tray in this application should not contact the gingival tissues in order to reduce the possibility of soft tissue irritation. The finished tray should fit snugly around the teeth for best results.

Use of the applique 150 is a significant advantage over conventional tray fabrication techniques, in that the applique 150 can be applied to a plurality of model teeth 46 at once and preferably to all of the model teeth 46 that correspond to the patient's teeth to be treated. As a result, application of a reservoir-making material to the surface of each model tooth 46 on an individual basis can be avoided and the total time required to make the tray is substantially reduced. The tray is preferably made with the applique 150 permanently bonded to the thermoplastic material, although as an alternative the applique 150 may be placed over the model teeth 46 with its protrusions facing outwardly (i.e. buccolabially) such that an impression of the applique 150 is formed in the thermoplastic material to create the support structures.

As illustrated in FIGS. 11 and 13, the applique 150 has a generally rectangular, strip-like configuration, although other configurations are also possible. For example, the applique may have a substantially straight upper edge to match the occlusal edges of the teeth 46, and a scalloped lower edge to match the shape of the gingival margin. In practice, however, satisfactory results have been obtained with the generally rectangular shape shown in FIGS. 11 and 13. Since the medication in the tray slowly escapes from the reservoir created by the applique 150 and contacts adjacent tooth structure while the tray is in use, substantially all of the buccolabial surfaces of the teeth underlying the applique 150 are subjected to the medication. For example, if the medication is a dental bleaching agent, the escape of the bleaching agent from the reservoir ensures that the entire buccolabial surface of each tooth is uniformly bleached to generally the same color, even though the reservoir does not extend over gingival portions of the buccolabial tooth surfaces.

In another embodiment, a continuous sheet containing the microreplicated surface (such as sheet 130 with surface 134) that has not been die cut is formed directly over the casting 40. The adhesive and release liner (such as adhesive 136 and release liner 138) are typically omitted in this embodiment. Consequently, the entire inner surface of the medication delivery tray (such as tray 12 in FIG. 9) contains the microreplicated surface. In one embodiment, the microreplicated surface may be constructed from a different material than backing layer (for example, backing layer 131). The softening point of the microreplicated surface may be greater than, less than or equal to the softening point of the backing layer, depending upon the application. For example, it may be desirable for some applications that the microreplicated structure is partially deformed during the molding process in order to better conform to the shape of the patient's dental structure. The continuous sheet with the microreplicated surface may be formed over the casting 40 or directly over the patient's dental structure. The medication (such as medication 128) may be applied to the entire inner surface of the medication delivery tray or to selective portions thereof.

Moreover, any of the techniques described above for making a dental tray may include as an option the use of a dental model that is made using digital data instead of a dental model that is cast from a dental impression. For example, a model arch similar to the casting 40 may be prepared by generating digital information defining the shape of the patient's upper dental arch, and then using the digital information to create the model. For example, the digital information may be created by the methods set out in PCT application no. WO 97/03622. In brief, PCT application no. WO 97/03622 describes a method of generating digital information of a patient's dental arches by making an impression of the patient's arches, and then removing a layer from the impression (or alternatively removing a layer from a model made from the impression) to obtain a flat surface; a video camera or other device is then used to collect digital data of the flat surface and the method is repeated; finally, the data is combined to provide a data set representative of the configuration of the patient's dental arches. Stereolithographic apparatus can then be used to make the model arch.

Other means for generating digital information of the patient's dental arch may also be employed. For example, the digital information may be generated electromechanically (e.g., stylus scanning), by laser scanning, by photogammetry, by sonic ranging, by digital video scanning or magnetically. Examples of devices for generating the information are described in an article by Rekow entitled *"Computer Aided Design and Manufacture in Dentistry: A Review of the State of the Art"*, from the Journal of Prosthetic Dentistry, Vol. 58, page 512 (1987). Other examples are described in U.S. Pat. Nos. 5,078,599, 5,131,844, 5,338,198, 4,611,288 and 5,372,502 as well as in an article entitled *"Three-dimensional dental cast analyzing system with laser scanning"* (Kuroda, et al., Am. J. Ortho. Dent. Othrop., Vol. 110 [4], October 1996, pages 365–69).

In yet another embodiment, any of the medication reservoir configurations discussed herein may be provided in a preformed or non-custom mouth tray. Some of the advantages of preformed or non-custom mouth trays include lower cost, immediate availability to the patient, and distribution through retail channels.

The medication delivery tray in accordance with the present invention is particularly suited for patients who desire to bleach their teeth. A common dental bleaching agent contains about 10% to about 16% carbamide peroxide, also called urea hydrogen peroxide, urea peroxide, hydrogen peroxide carbamide and perhydrol-urea. Carbamide peroxide has been used by dental clinicians since the 1960's as an oral antiseptic. Tooth whitening was a side effect of extended contact time. Over the counter ("OTC") compositions of 10% carbamide peroxide are available as "Gly-Oxide" by Marion Laboratories and "Proxigel" by Reed and Carnrick. A preferred dental bleaching agent comprises 64.86% propylene glycol, 21.00% glycerol, 1.5% carboxypolymethylene polymer (e.g. Carbapol brand No. 980), 2.34% tris amino, 0.30% mint flavor and 10.00% carbamide peroxide, with the viscosity increased by adjusting the pH to about 5.8.

The complete disclosures of all patents, patent applications, and publications mentioned above are incorporated herein by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A medication delivery tray for delivering medication to dental structures of a patient, comprising:
    a dental tray comprising a base, a buccal wall and a lingual wall defining an inner surface; and
    at least one applique in the dental tray, each applique comprising a plurality of discrete support members and presenting at least one reservoir, the support members arranged to resist the flow of medication from the medication reservoir in a gingival direction and extending toward the dental structures of the patient when the delivery tray is placed over the patient's teeth.

2. The medication delivery tray of claim 1 wherein the applique comprises a hydrophilic material.

3. The medication delivery tray of claim 1 wherein the medication reservoir extends over substantially the entire inner surface of the medication delivery tray.

4. The medication delivery tray of claim 1 wherein the medication reservoir is located on the inner surface of the medication delivery tray.

5. The medication delivery tray of claim 1 wherein the support members are selected from a group consisting of cubes, rods, cones, truncated cones, pyramids, truncated pyramids, semispheres, cylinders, nail heads, and mushroom-shaped members.

6. The medication delivery tray of claim 1 wherein the plurality of discrete support members are arranged to define a tortuous path.

7. The medication delivery tray of claim 6 wherein the tortuous path resists the flow of medication in a direction along at least one of a mesial-distal direction and a gingival direction.

8. The medication delivery tray of claim 1 wherein the medication reservoir extends over at least one of a tooth or gum tissue when the medication delivery tray is retained by the dental structure of a patient.

9. The medication delivery tray of claim 1 wherein the dental tray comprises a custom dental tray.

10. The medication delivery tray of claim 1 wherein the dental tray comprises a dental bleaching tray.

11. A kit for forming a medication delivery tray from a thermoplastic material molded over a dental structure or a casting thereof, comprising a sheet of thermoplastic material and at least one applique attachable to the dental structure or casting thereof for forming at least one medication reservoir in the thermoplastic material, each applique defining a plurality of support members selected from a group consisting of cubes, rods, cones, truncated cones, pyramids, truncated pyramids, semispheres, cylinders, nail heads and mushroom-shaped members and arranged to resist the flow of medication from the medication reservoir in a gingival direction.

12. The kit of claim 11 wherein each applique is configured to be embedded in the thermoplastic material.

13. The kit of claim 11 wherein each applique is configured to form the medication reservoir and support members integrally in the thermoplastic material.

14. A kit for forming a medication delivery tray comprising a sheet of thermoplastic material moldable over a patient's dental structure or a casting thereof, the sheet member comprising a backing layer and a plurality of support members projecting from the backing layer and arranged to resist the flow in a gingival direction of medication from the medication delivery tray formed therefrom, wherein the backing layer comprises a material different than the support member material.

15. A method of making a medication delivery tray for delivering medication to dental structures of a patient comprising the acts of:
    applying at least one applique to a model of the patient's dental structure, each applique defining a plurality of support members arranged to resist the flow of medication from the medication reservoir in a gingival direction;
    forming a custom dental tray over the model and each applique from a thermoplastic material; and
    removing the custom dental tray from the model.

16. The method of claim 15 wherein each applique is embedded into the thermoplastic material after the custom dental tray is removed from the model such that the support members project toward the dental structures of the patient when the tray is placed on the dental structures.

17. The method of claim 15 wherein each applique remains on the model after the custom dental tray is removed.

18. The method of claim 15 wherein the support members are selected from a group consisting of cubes, rods, cones, truncated cones, pyramids, truncated pyramids, semispheres, cylinders, nail heads, and mushroom-shaped members.

19. The method of claim 15 wherein the support members are arranged to define a tortuous path.

20. The method of claim 15 further comprising the acts of:
    applying a medication to areas adjacent the support members; and
    applying the custom mouth tray to the patient's dental structure such that the support members are positioned opposite at least a portion of the dental structure.

21. The method of claim 20 wherein the act of applying a medication includes the act of applying a dental bleaching agent.

22. The method of claim 15 wherein the act of applying at least one applique to a model of the patient's dental structure includes the act of applying a single applique over a plurality of teeth of the model.

23. The method of claim 22 wherein the single applique has an elongated, generally rectangular configuration.

24. A method of making a medication delivery tray for delivering medication to dental structures of a patient comprising the acts of:

preparing a sheet member comprising a backing layer and a plurality of support members projecting from the backing layer;

forming the sheet member over a model of the patient's dental structure to provide a custom dental tray such that the support members are arranged to resist the flow of medication from the medication delivery tray in a gingival direction; and removing the custom dental tray from the model.

25. A method of making a medication delivery tray for delivering medication to dental structures of a patient, comprising the acts of:

providing a model of at least a portion of a dental arch;

applying an applique over a plurality of teeth of the model; and forming a custom dental tray over the model and the applique; and removing the tray from the model, wherein the applique is affixed to the thermoplastic material as the tray is removed from the model.

26. The method of claim 25 wherein the support members are selected from a group consisting of cubes, rods, cones, truncated cones, pyramids, truncated, pyramids, semispheres, cylinders, nail heads or mushroom-shaped members.

27. The method of claim 26 where in the support members are arranged to define a tortuous path.

28. A method of making a medication delivery tray for delivering medication to dental structures of a patient, comprising the acts of:

providing a model of at least a portion of a dental arch;

applying an applique over a plurality of teeth of the model; and forming a custom dental tray over the model and the applique, wherein the applique includes a plurality of support members arranged to resist the flow of medication.

29. A method of whitening teeth including the method of making a medication delivery tray according to claim 28 and also including the act of applying a dental bleaching agent to the tray.

* * * * *